United States Patent [19]

Singh et al.

[11] 4,275,160

[45] Jun. 23, 1981

[54] IMIPRAMINE DERIVATIVES AND POLY(AMINO ACID) CONJUGATES

[75] Inventors: Prithipal Singh; Marcel R. Pirio, both of Sunnyvale, Calif.

[73] Assignee: Syva Company, Palo Alto, Calif.

[21] Appl. No.: 55,419

[22] Filed: Jul. 6, 1979

[51] Int. Cl.³ .......................... C07G 7/00; C12N 9/96
[52] U.S. Cl. ............................... 435/188; 260/112 R; 260/112 B; 260/121; 260/239 BB; 424/85; 424/88; 435/7; 525/420
[58] Field of Search ............... 435/188, 7; 260/112 R, 260/121, 112 B; 424/85, 88; 525/420

[56] References Cited

U.S. PATENT DOCUMENTS

| | | | |
|---|---|---|---|
| 4,058,511 | 11/1977 | Singh | 424/88 X |
| 4,083,948 | 4/1978 | Davis et al. | 260/112 R X |
| 4,104,379 | 8/1978 | Gallagher, Jr. et al. | 435/188 X |

OTHER PUBLICATIONS

J. Anal. Tox. 1, pp. 236–243, (1977), Kaul et al.

*Primary Examiner*—Howard E. Schain
*Attorney, Agent, or Firm*—Bertram I. Rowland

[57] ABSTRACT

Imipramine functionalized compounds are provided for conjugation to antigenic compounds, particularly poly(amino acids), and enzymes. The antigenic conjugates are employed for the production of antibodies, which find particular use in immunoassays for the determination of imipramine, while the enzyme conjugate finds use in a homogeneous enzyme assay for the determination of imipramine.

15 Claims, No Drawings

IMIPRAMINE DERIVATIVES AND POLY(AMINO ACID) CONJUGATES

BACKGROUND OF THE INVENTION

Imipramine (a dibenzazepine derivative) finds extensive use for the treatment of depression. In administering imipramine, it is frequently necessary to ensure that the imipramine blood level remains within a certain narrow concentration range, in order to insure effective dosage, while avoiding levels which may be toxic or produce undesirable effects.

A number of techniques have been developed for determining imipramine, either based on extraction of a blood sample and determination of fluorescence of the extract or by chromatographic methods, such as thin layer chromatography or high pressure liquid chromatography. All of these methods have various inadequacies in either requiring extremely careful clinician handling, being slow, or subject to substantial interference from other constituents present in serum. Also, depending on the method of extraction, metabolites may be included to a greater or lesser degree in the extract.

It is therefore desirable to provide a simple and rapid procedure for determining imipramine levels in serum or other physiological fluids, which provides reproducible values and assurances of the compounds which are being measured.

BRIEF DESCRIPTION OF THE PRIOR ART

Imipramine is closely related chemically to amitriptyline and nortriptyline. Techniques reported for the determination of amitriptyline in biological fluids include the use of thin layer chromatography, gas-liquid chromatography and GLC-mass spectrometry. Gifford, et al., *J. of Chrom.*, 105, 107–113 (1975); Gupta, et al., *Clin. Biochem.*, 9, 247–51 (1976); Nyberg and Martensson, *J. Chrom.*, 143, 491 (1977); Watson and Steward, *J. Chrom.*, 134, 182 (1977); ibid 132 155–159 (1977). Radioimmunoassay has been reported for amitriptyline by Aherne, et al., *Br. J. Clin. Pharmac.*, 3, 561 (1976), Turner, *Lancet*, 108, 1316 (1977); and Aherne, et al., *Lancet* 1214 (1977). In Aherne, et al., ibid, a synthesis for an antigen for antibody formation is described, where nortriptyline is substituted with aminobutylene followed by conjugation to bovine serum albumin employing carbodiimide. In another antigen conjugate synthesis by Kaul, et al., *J. Anal. Tox.*, 1, 236 (1977), nortriptyline was conjugated to bovine serum albumin through a succinic group. The resulting antibodies were found to have significant cross-reactivity with a number of other tricyclic drugs.

SUMMARY OF THE INVENTION

A synthetic procedure is provided for preparing non-oxo-carbonyl containing derivatives of imipramine for conjugation to antigenic materials, particularly poly(amino acids) and enzymes. The antigenic conjugate is employed for the production of antibodies for use in immunoassays. The enzyme conjugate is employed as a reagent for the determination of imipramine in immunoassays. The antibodies and enzyme conjugates are provided in combination in kits to be used for the rapid and accurate determination of imipramine in serum as well as other physiological fluids.

DESCRIPTION OF THE SPECIFIC EMBODIMENTS

Novel compounds are provided which are imipramine derivatives having a non-oxo-carbonyl functionality (including the nitrogen and sulfur analogs thereof) for linking imipramine at the 10-position to poly(amino acids), which are antigenic, or enzymes. The antigenic conjugates are employed for the production of antibodies which are specific for imipramine, the antibodies finding use in immunoassays. The enzyme conjugates are employed as a reagent in homogeneous enzyme immunoassays for the determination of imipramine.

The imipramine precursors employed for conjugation to poly(amino acids) will have from about 14 to 30 carbon atoms, usually 18 to 28 carbon atoms and preferably 19 to 24 carbon atoms, having in addition to the nitrogen in the tricyclic structure, 1 to 8, usually 2 to 6, and preferably 2 to 4 heteroatoms which are chalcogen (O and S) or nitrogen, preferably oxygen. The preferred linking functionality is non-oxo-carbonyl (including the nitrogen and sulfur analogs thereof). Oxygen is present as carbonyl, oxo or non-oxo, or oxy. Sulfur is present as thiono or thio and nitrogen is present as amino bonded solely to carbon or amido.

For the most part, compounds of this invention will have the following formula:

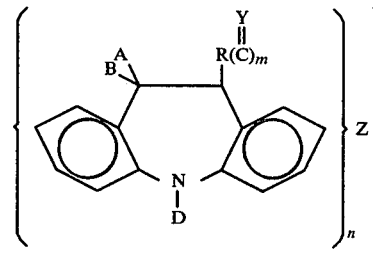

wherein:
D is 3-dimethylaminopropylene;
A and B are hydrogen or are taken together to form oxo, and are H when Z is poly(amino acid);
R is a linking group, which is an aliphatic group of from 1 to 8 carbon atoms, usually 2 to 6 carbon atoms, and from 0 to 2, usually 0 to 1 hetero atoms which are O, N, and S, where O and S are bonded solely to carbon and N is either bonded solely to carbon or is amido; R is preferably hydrocarbon having 0 to 1 site of unsaturation, e.g. ethylenic, and terminates in methylene bonded to Z when m is 0;
Y is O, S or NH, preferably O;
Z is hydrogen; oxy including hydroxyl, alkoxyl of from 1 to 6 carbon atoms, or an activated ester capable of amide formation in an aqueous medium, e.g. N-oxy succinimide and p-nitrophenoxy, or a poly(amino acid), which is antigenic or an enzyme, which poly(amino acid) is joined by a bond to a methylene group when m is 0 and by an amide (includes amidine) bond when m is one;
m is 0 or 1 when Z is a poly(amino acid) and is otherwise one;
n is 1 when Z is other than a poly(amino acid) and is otherwise 1 to the molecular weight of Z divided by 500, more usually divided by 1,000 and frequently divided by 1,500, generally ranging from 1 to 500, preferably from 10 to 100, when Z is an antigen, and from 1 to 30, more usually 2 to 20, and preferably from 2 to 16, when Z is an enzyme.

Preferred R groups include alkylenes, such as ethylene, propylene, butylene, pentylene, hexylene, heptylene, octylene, 2-methylpropylene, etc., alkenylenes such as 2-butenylene, 2-pentenylene, vinylene, etc., and oxyalkylenes and oxyalkenylenes such as ethyleneoxymethylene, ethyleneoxyethylene, 1-methyleneoxy-2-propenylene, heptyleneoxyethylene, etc.

For those compounds where n is one, the compounds will be of the formula:

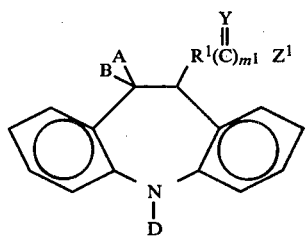

wherein D and Y have been defined previously;

A and B are H or are taken together to form oxo;

$R^1$ is the same as R, but is preferably alkylene of from 1 to 7 carbon atoms;

$m^1$ is one;

$Z^1$ is hydrogen, hydroxyl, alkoxyl of from 1 to 6, more usually from 1 to 3 carbon atoms, particularly methyl and ethyl, an oxy group forming an activated ester which readily reacts with the amine group of poly(amino acids) under mild conditions in an aqueous medium to form amides, such as N-oxy succinimide or p-nitrophenyl.

Where Z is a poly(amino acid), the compounds will for the most part have the following formula:

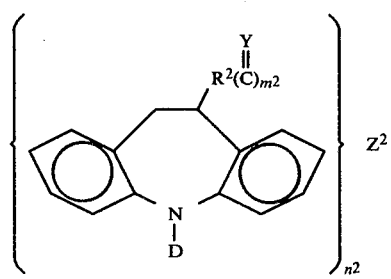

wherein D and Y have been defined previously;

$R^2$ is the same as $R^1$;

$Z^2$ is poly(amino acid), which is either antigenic or an enzyme;

$m^2$ is 0 or 1, preferably 1; and $n^2$ is at least 1, and usually greater than 1;

when $Z^2$ is antigenic, $n^2$ will normally be at least 2, and not greater than the molecular weight of $Z^2$ divided by 500, usually not greater than the molecular weight of $Z^2$ divided by 1,000, and preferably not greater than the molecular weight of $Z^2$ divided by 1,500, generally ranging from 2 to 500; when $Z^2$ is an enzyme, $n^2$ will be at least 1, usually not greater than 30, more usually in the range of 2 to 20, and preferably in the range of about 2 to 16.

The poly(amino acids) will generally range from about 5,000 molecular weight, having no upper molecular weight limit, normally being less than 10,000,000 usually not more than about 600,000. There will usually be different ranges, depending on whether an antigen or an enzyme is involved, with antigens ranging from about 5,000 to $10^7$, usually from about 20,000 to 600,000, and more usually from about 25,000 to 250,000 molecular weight; while enzymes will generally range from about 10,000 to 600,000, more usually from about 10,000 to 300,000 molecular weight. There will usually be at least about one conjugate per 500,000 molecular weight, more usually at least one per 50,000 molecular weight. With intermediate molecular weight antigens (35,000 to 1,000,000), the number of conjugate groups will generally be from about 2 to 250, more usually from 10 to 100. With lower molecular weight antigens, below 35,000, the number of conjugates will generally be in the range of from about 2 to 10, usually in the range of 2 to 5.

Various protein types may be employed as the antigenic material. These types include albumins, serum proteins, e.g., globulins, ocular lens proteins, lipoproteins, etc. Illustrative proteins include bovine serum albumin, keyhole limpet hemocyanin, egg ovalbumin, bovine γ-globulin, etc. Alternatively, synthetic poly(amino acids) may be prepared having a sufficient number of available amino groups, e.g., lysines.

The enzymes can be varied widely, depending upon the rapidity with which one desires a result and the physiological fluid in which the imipramine is to be measured. Primarily, the enzymes of choice, based on the I.U.B. classification are: Class 1. Oxidoreductases and Class 3. Hydrolases. Particularly in Class 1, the enzymes of interest are dehydrogenases of Class 1.1, more particularly 1.1.1 and 1.1.99 and peroxidases, in Class 1.11. Of the hydrolases, particularly Class 3.1, more particularly 3.1.3 and Class 3.2, more particularly 3.2.1.

Illustrative dehydrogenases include malate dehydrogenase, glucose-6-phosphate dehydrogenase, and lactate dehydrogenase. Of the peroxidases, horse radish peroxidase is illustrative. Of the hydrolases, alkaline phosphatase, β-galactosidase, β-glucosidase and lysozyme are illustrative.

Particularly preferred are those enzymes which employ nicotinamide adenine dinucleotide (NAD) or its phosphate (NADP) as a cofactor, particularly the former. Most preferred as the choice of enzyme is glucose-6-phosphate dehydrogenase.

The synthetic scheme for preparing the subject compounds is set forth in the following flow chart:

CHART 1

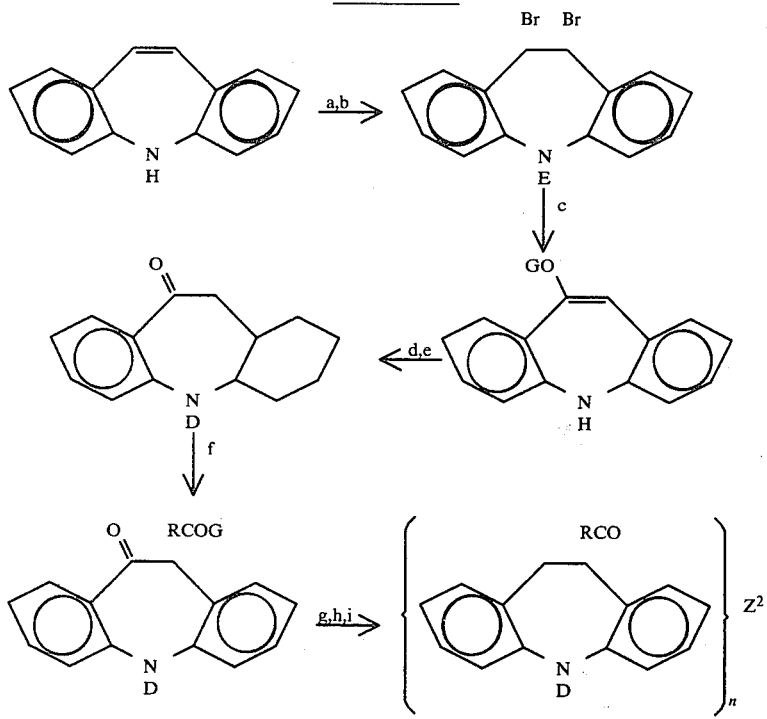

- a    EJ, E is alkanoyl of from 1 to 6 carbon atoms and J is an activating group, such as halo, acyloxy or activating ester
- b    $Br_2$
- c    NaOG, GOH, G is alkyl of from 1 to 3 carbon atoms
- d    DW, $NaNH_2$, W is replaceable halogen, atomic number of 17 to 35
- e    $H^{\oplus}$
- f    $WRCO_2G$, $H^{\ominus}$ In carrying out the preparation of the compositions of this invention dibenzazepine is combined with pyridine and acetyl halide in an anhydrous benzene solution. Bromine is then added to the acetyl derivative of dibenzazepine followed by base elimination which also removes the acetyl group. The annular nitrogen is substituted with the 3-dimethylamino propyl group and the product is then hydrolyzed to introduce an oxo group at C-11. The C-10 carbanion is generated with base, and then combined with a haloaliphatic carboxylic ester for substitution at C-10 of the dibenzazepine followed by reductive removal of the carbonyl. The ester is hydrolyzed and the carboxyl is then activated and condensed with a poly(amino acid).

By employing the above procedure imipramine is functionalized to a compound which can be conjugated to poly(amino acids), either antigenic or enzymes. The structure of imipramine is retained during the synthetic procedure and those elements of the structure which provide for distinctions between closely similar compounds are exposed to allow for formation of antibodies which are capable of distinguishing imipramine from similarly structured compounds. The antigenic compounds may be injected into a wide variety of vertebrates in accordance with conventional methods for the production of antibodies. Usually the animals are bled periodically with successive bleeds having improved titer and specificity, then plateauing and diminishing in their specificity and titer.

As previously indicated, the antibodies and enzyme reagents prepared in accordance with the subject invention find particular use in immunoassays for the determination of imipramine. A description of the method for carrying out the immunoassay, which is a homogeneous enzyme immunoassay, may be found in U.S. Pat. No. 3,817,837. The method involves combining the enzyme conjugate, the unknown sample suspected of containing imipramine, and an antibody for imipramine in an aqueous buffered medium at temperatures in the range of about 10° to 50° C., more usually from about 20° to 40° C., and determining the enzyme activity as compared to the enzyme activity of an assay medium having a known amount of imipramine.

The following examples are offered by way of illustration and not by way of limitation.

(All temperatures not otherwise indicated are in centigrade. All parts and percents are by weight except for mixture of liquids which are by volume.)

EXPERIMENTAL

Ex. 1. Preparation of 5-acetyl-5H-dibenz[b,f]azepine

In a 500 ml round bottom flask fitted with a stirrer, dropping funnel and calcium chloride drying tube was placed recrystallized dibenz[b,f]azepine (33.5 g, 0.173 moles), 200 ml of anhydrous benzene and pyridine (13.6 g, 0.173 moles). Acetyl chloride (~12.3 ml) was then added dropwise to the mixture. A white precipitate formed with disappearance of orange color. After 3 to 4 hours of stirring, the reaction mixture was extracted with three 100 ml portions of 10% hydrochloric acid or until the extract remained acidic. The organic phase was washed with 5% Na2CO3 in water, dried over anhydrous magnesium sulfate, filtered and concentrated. Crystallization from a hexane-chloroform mixture afforded 49 g of 5-acetyl-5H-dibenz[b,f]azepine, m.p. ~121°.

Ex. 2. Synthesis of 5H-acetyl-10,11-dibromo-10,11-dihydrodibenz[b,f]azepine

In a 250 ml round bottom flask equipped with a magnetic stirrer was placed 25 g (0.106 moles) of 5-acetyl-5H-dibenz[b,f]azepine prepared in Example 1 and 100 ml of chloroform. The solution was cooled in an ice-bath to 5°–10° and 16.9 g (0.106 moles) of bromine in 25 ml of chloroform was added dropwise. After the addition was completed, the light orange solution was stirred for an additional 0.5 hours, then decolorized with large amounts of Norit A and filtered through a Celite pad. This was repeated until the solution was clear. The volume was reduced to 100 ml and was allowed to crystallize overnight at 0°. Crystal clear plates were collected and dried under vacuum leaving 37 g of a white solid, m.p. 136°–137°.

Ex. 3 Preparation of 10-methoxy-5H-dibenz[b,f]azepine

In a 500 ml three-neck round bottom flask equipped with a magnetic stirrer and reflux condenser (the exit connected to a dry nitrogen source) was placed 304 ml of absolute methanol and 18.2 g (0.76 moles) of small pieces of clean sodium metal added at a rate to maintain constant reflux. After all the metal had reacted the solution was cooled to room temperature. 5H-Acetyl-10,11-dibromo-10,11-dihydro-5H-dibenz[b,f]azepine (37 g, 0.094 moles) prepared in Example 2 was added at once and refluxed for 16 hours, after which time 150 ml of methanol was distilled off followed by refluxing for an additional 24 hours. Water (150 ml) was added to the warm solution and the yellow solid which precipitated was filtered and dried leaving 36 g of crude product. This solid was dissolved in chloroform, the solution filtered to remove undissolved impurities, concentrated and finally the product crystallized from absolute ethanol affording a yellow solid, m.p. 124°.

Ex. 4. Preparation of 5-(3'-Dimethylaminopropyl)-10-methoxy-5H-dibenz[b,f]azepine A 500 ml round bottom flask containing 9.87 g (0.044 moles) of 10-methoxy-5H-dibenz[b,f]azepine prepared in Example 3 and 13.9 g (0.088 moles) of 3-dimethylaminopropylchloride was evacuated for several days. Anhydrous toluene (250 ml) was added followed by 7.04 g (0.176 moles) of sodium amide. The heterogeneous solution was stirred at ambient temperature for a few minutes and then refluxed for 16 hours. After 16 hours of refluxing, tlc analysis of the reaction mixture (silica gel GF plates, methanol:chloroform 1:9; visualized under UV lamp and sulfuric acid-ceric sulfate spray) revealed that the reaction was complete and that no starting material remained. Enough water was added to slowly decompose the excess sodium amide. The dark-brown solution was placed in a 1 liter separatory funnel and extracted with four 250 ml portions of water. The organic phase was dried over anhydrous magnesium sulfate, charcoal was added and the mixture was filtered through a Celite pad. The filtrate was concentrated leaving a brown oil (12.6 g).

Ex. 5. Hydrolysis of 5-(3'-dimethylaminopropyl)-10-methoxy-5H-dibenz[b,f]azepine 5-(3'-Dimethylaminopropyl)-10-methoxy-5H-dibenz[b,f]azepine prepared in Example 4, (11.6 g, 0.037 moles), 100 ml of 1 N HCl and 140 ml of tetrahydrofuran were combined. The brown reaction mixture was allowed to stir at ambient temperature overnight (~14 hours).

Tlc (silica gel GF plates, methanol:chloroform 1:9) indicated a very small amount of methyl vinyl ether remaining and the presence of a small amount of unknown fluorescent material (visualized under UV lamp). The reaction mixture was neutralized with solid sodium carbonate pH~7 and brought up to a volume of 300 ml with water. The aqueous media was extracted with three 500 ml of dichloromethane. The combined organic phases were dried with magnesium sulfate, filtered and concentrated on a rotary vaporator leaving a brown oil, (~10 g). This crude material was applied atop a dry chromatography column (5×60 cm) containing 450 g of 60–200 mesh Baker-silica gel, which had been preequilibrated with 10% by weight of methanol chloroform 1:9 (3 hrs rotating the mixture on a rotary evaporator). The column was eluted (methanol:chloroform 1:9) and 25 ml increments were collected. The eluents were monitored by tlc and the appropriate fractions were pooled, yielding upon concentration, 8.2 g of 5-(3'-dimethylaminopropyl)-10,11-dihydro-5H-dibenz[b,f]azepine-10-one. The remaining impure fractions were pooled and concentrated to yield 2.0 g and then chromatographed. (10–20×20 cm 25 prep tlc silica PF-254 plates, methanol:chloroform 1:9). Appropriate bands were collected by visualization under a UV lamp. The material was extracted from silica with a 3:7 methanol:chloroform solution. The filtrate was concentrated on a rotary evaporator, and dried under vacuum with mild heating, yielding 1.3 g of 5-(3'-dimethylaminopropyl)-10,11-dihydro-5H-dibenz[b,f]azepine-10-one. The total material recovered was 9.5 g.

Ex. 6. Alkylation of 5-(3'-dimethylaminopropyl)-10,11-dihydro-5H-dibenz[b,f]azepine-10-one In a dry 100 ml three-neck round bottom flask, into which a steady stream of argon was passed, were placed 0.547 g (0.0228 moles, 50% oil dispersion) sodium hydride and 20 ml of dry dimethoxyethane. The solution was stirred with a magnetic bar. The sodium hydride was allowed to settle while the solvent was pipetted to remove excess oil. This was repeated twice. A fresh 15 ml of dry dimethoxyethane was added followed by a 25 ml dimethoxyethene solution of 1.70 g (0.0057 moles) 5-(3'-dimethylaminopropyl)-10,11-dihydro-5H-dibenz[b,f]azepine-10-one. The solution was stirred under positive argon pressure at ambient temperature for one hour during which time the solution turned red. This was followed by dropwise addition of 2.75 g (0.0114 moles) of ethyl-4-iodobutyrate in 20 ml of dry solvent. After an hour of stirring the reaction progress was monitored by tlc (silica gel-GF plates, methanol:chloroform 1:9) which indicated that the reaction was near completion (visualization with UV short/long wavelength light and sulfuric acid-ceric sulfate spray).

Water (50 ml) was slowly added to the reaction mixture, followed by 150 ml of 20% acetic acid. This solution was extracted with two 100 ml portions of ethyl ether and the organic phase was back extracted with dilute acetic acid. The aqueous phase was combined and brought to pH~8 with solid sodium hydroxide. The solution was then extracted with two 150 ml portions of chloroform, dried with magnesium sulfate, filtered and concentrated without heating on the rotary evaporator with reduced pressure to yield 2.8 g of light brown oil. One half of the material (1.4 g) was chromatographed (12-20×20 cm 2.5 mm prep tlc silica gel PF-254, 366 plates, methanol:chloroform 1:9). The appropriate band was marked using a UV lamp, collected, extracted with absolute methanol, filtered and then concentrated to yield 1 g of pure 10-carboethoxypropyl-5-(3'-dimethylaminopropyl)-5H-dibenz[b,f]azepine-11-one.

Ex. 7. Hydrogenolysis of 10-carboethoxypropyl-5-(3'-dimethylaminopropyl)-5H-dibenz[b,f]azepine-11-one In a 150 ml glass hydrogenation vessel were placed 1 g (2.45 mole) of the 10-carboethoxypropyl-5-(3'-dimethylaminopropyl)-5H-dibenz[b,f]azepine-11-one prepared in Example 6 dissolved in 35 ml of glacial acetic acid and 1 g of 10% palladium on carbon. The vessel was placed on a Parr-pressure apparatus, flushed with nitrogen, evacuated, pressurized to 60 psi hydrogen and shaken for 4 days with daily pressure adjustment. The vessel was then flushed with nitrogen, evacuated, filtered through a Celite pad, washed with absolute methanol and concentrated on a rotary evaporator under reduced pressure. The residue was dissolved in chloroform and extracted with 10% $NaHCO_3$ to remove excess acid. The organic phase was dried with magnesium sulfate, filtered and concentrated. The reaction was repeated on another 1 g lot of 10-carboethoxypropyl-5-(3'-dimethylaminopropyl)-5H-dibenz[b,f]azepine-11-one prepared in Example 6. The products were combined yielding 1.6 g crude material. The 1.6 g was applied to chromatographic plates (20–20 cm 2.5 mm prep tlc plates silica gel PF-254) and eluted with diethyl ether saturated with ammonia gas. The plates were air dried and developed four times until separation was maximized by UV inspection. The two bands were isolated, extracted with methanol, concentrated, redissolved in chloroform, filtered and concentrated on a rotary evaporator yielding 0.600 g of 10-carboethoxypropyl-5-(3'-dimethylaminopropyl)-10,11-dihydro-5H-dibenz[b,f]azepine and 0.805 g of starting material. The product (0.600 g) containing trace amounts of starting material was rechromatographed (using silica gel PF-254 20×20 cm 2.5 mm prep plates) and eluted with methanol:chloroform 1:9. The isolation procedure was the same as above.

Ex. 8. Saponification of 10-carboethoxypropyl-5-(3'-dimethylaminopropyl)-10,11,-dihydro-5H-dibenz[b,f]azepine 5-(3'-Dimethylaminopropyl)-10,11-dihydro-5H-dibenz[b,f]azepine-10-one (450 mg, 1.14 mmoles), 30 ml of methanol, 10 ml 1 N sodium hydroxide and 10 ml of THF were stirred overnight at ambient temperature. Tlc analysis (silica gel GF-methanol:chloroform 1:9) revealed that the reaction was complete. The reaction was neutralized with dilute hydrochloric acid to pH~7.0 and then concentrated on a rotary evaporator followed by drying under high vacuum. The solid material was extracted with methanol:chloroform (1:4) and the filtrate was monitored until all the amino acid was removed from the salts. The light yellow filtrate was concentrated, chromatographed (10–20×20 cm 25 silica gel PF-254 prep tlc plates) and eluted with absolute methanol. The appropriate band was isolated by UV visualization and extracted from the absorbent with absolute methanol. The filtrate was concentrated, redissolved in chloroform, filtered, concentrated and dried under high vacuum to yield a white foam weighing 400 mg.

Ex. 9. Conjugation of BSA with 10-carboethoxypropyl-5-(3'-dimethylaminopropyl)-10,11-dihydro-5H-dibenz[b,f]-azepine In a 10 ml round bottom flask equipped with a calcium chloride drying tube were placed 0.171 g (0.468 mmoles) of dry 10-carboethoxypropyl-5-(3'-dimethylaminopropyl)-10,11-dihydro-5H-dibenz[b,f]azepine prepared in Example 8, 96.5 mg (0.468 mmoles) of distilled N,N-dicylohexylcarbodiimide, 53.8 mg (0.468 mmoles) of recrystallized N-hydroxysuccinimide (NHS) and 5 ml of anhydrous dimethylformamide. The solution was stirred at 5°–10° for 20 hours. Within a short time interval a white precipitate appeared. The reaction mixture was passed through a glass wool plug and into a stirring solution of 0.5 g ($7.8 \times 10^{-6}$ moles) of bovine serum albumin (BSA) (lot 36 Miles-Pentex) dissolved in 40 ml of 0.1 M $Na_2CO_3$-$NaHCO_3$ buffer (pH~9.8) at 5°. The clear protein solution became slightly turbid upon addition of the NHS ester solution. The mixture was allowed to stir in the cold overnight (~18 hours) after which the conjugate was centrifuged for 15 minutes at 10,000 rpm. The supernatant was dialyzed in a cylinder (m.w. cut off of 6,000–8,000; dia. 14.6 mm) against 6 liters of 1 M $Na_2CO_3$-$NaHCO_3$ buffer pH~9.8 overnight (~12 hours), followed by successive solvent changes (3×6 liter $NH_4OH$—$H_2O$ solution, pH9.6) for four hours each. The solution was passed through a Sephadex-medium G-50 column (approximate volume four times the conjugate solution). The fractions were pooled and filtered through 0.22 μm millipore filter into a sterilized lyophilization flask to yield upon drying 400 mg of the conjugate. Calculation of the hapten/protein ratio gave 20 by molar absorptivity differences.

Ex. 10. Conjugation of BgG with 10-carboethyoxypropyl-5-(3'-dimethylaminopropyl)-10,11-dihydro-5H-dibenz[b,f]-azepine In a 20 ml round bottom flask, fitted with a calcium chloride drying tube were placed 193 mg (0.529 mmoles) of dry 10-carboethoxypropyl-5-(3'-dimethylaminopropyl)-10,11-dihydro-5H-dibenz[b,f]azepine prepared in Example 8, 109 mg (0.529 mmoles) of distilled N,N-dicyclohexylcarbodiimide, 60.8 mg (0.529 mmoles) of recrystallized N-hydroxysuccinimide and 8 ml of anhydrous dimethylformamide. The solution was stirred at 5° for 24 hours. Analysis using Avicel F (cellulose 250 microns) revealed NHS ester formation under UV light (eluant 10% DMF-$CHCl_3$). The NHS ester solution was conjugated to Miles-Pentex Bovine Gamma Globulin (BgG) Fraction II Lot 67 by first being passed through a glass wool plug directly into a stirring 50 ml 0.1 M $Na_2CO_3$-$NaHCO_3$ buffer (pH9.8) solution of 0.50 g ($2.9 \times 10^{-6}$ moles) BgG. The clear solution began to turn turbid and was kept in the cold for 22 hours. The conjugate was dialyzed in a cylinder (m.w. cutoff 6,000–8,000; dia 14.6 mm) against successive changes; first, 6 liters 0.1 M $Na_2CO_3$—$NaHCO_3$ buffer pH9.8 for 18 hrs, followed by 4×6 liters $NH_4O$-

H—H₂O pH9.8 solutions for ~4 hours each. At this point a heavy precipitate had formed in the cylinders. The solution was passed through a Sephadex G50 medium, column (volume was approximately four times the volume of protein solution). Appropriate fractions were combined and slowly filtered through 0.22 μm millipore filter using pressure. The clear antigen solution upon lyophilization yielded 200 mg of conjugate. Calculation of the hapten/protein ratio by molar absorptivity differences was 30.

Ex. 11. Conjugation of 10-(3'-carboxypropyl)-5-(3-dimethylaminopropyl)-10,11-dihydro-5H-dibenz[b,f]azepine with glucose-6-phosphate Dehydrogenase Into a dry reaction flask was introduced 11 mg (30μ moles) of the 10-(3'-carboxypropyl)imipramine prepared in Example 8, 3.70 mg of N-hydroxysuccinimide, 6.62 mg of ethyl dimethylaminopropyl carbodiimide and 75 μl of dry DMF and agitated at 4° overnight to provide the desired ester (0.4μ mole/ml).

Into a reaction flask was introduced 0.5 ml G-6-PDH (Beckman lot H01, 2.5 mg/ml), 20.25 mg glucose-6-phosphate Na₂, 20.98 mg NADH and 150 μl carbitol in 3×50 μl additions. Three 1 μl additions of the above solution were made over a period of about 1.5 hrs, with a total reaction time of about 2 hrs.

The reaction product was chromatographed on a Sephadex G-50 column and eluted 0.055 tris-HCl buffer, pH8.1 and collected at 30 drops per fraction for the first 12 fractions and 20 drops per fraction for the next 28 fractions. Fractions 12–19 were pooled to yield 11.5 ml. The enzyme conjugate had 46.7% of the original activity of the enzyme and was 67% inhibitable with a saturating amount of antiimipramine sera.

In accordance with the above results, the compositions of the present invention provide for reagents which can be used in a sensitive immunoassay which is highly specific for imipramine and imipramine related metabolites. Thus a rapid accurate method is provided for the determination of imipramine, which can be used in therapeutic dosage monitoring. The simplified method allows for the monitoring of patients to ensure that a therapeutic dosage is applied.

The synthetic procedure provides for the preparation of imipramine derivatives without substantial modification of the structure which would have resulted in a loss of specificity of the antibodies and the enzyme reagent. Thus a synthetic route is provided to produce antibodies which are specific for imipramine.

Although the foregoing invention has been described in some detail by way of illustration and example for purposes of clarity and understanding, it will be obvious that certain changes and modifications may be practiced within the scope of the appended claims.

What is claimed is:

1. Compound of the formula:

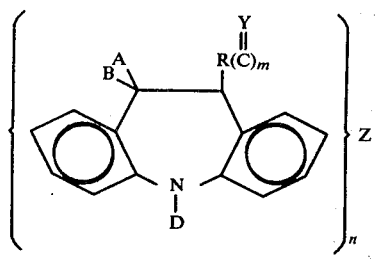

wherein:
D is 3-dimethylaminopropylene;
A and B are each H;
R is an aliphatic linking group of from 1 to 8 carbon atoms;
Y is O, S or NH;
Z is a poly(amino acid);
m is 0 or 1; and
n is in the range of one to the molecular weight of Z divided by 500.

2. Compound according to claim 1 wherein R has from 0 to 1 site of aliphatic unsaturation and from 0 to 2 hetero atoms which are O, N and S where O and S are bonded solely to carbon and N is bonded solely to carbon or is amido.

3. Compound according to claim 2 wherein Z is an antigen and n is in the range of from 1 to 500.

4. Compound according to claim 2 wherein Z is an enzyme and n is from 1 to 30.

5. Compound according to claim 1 and of the formula:

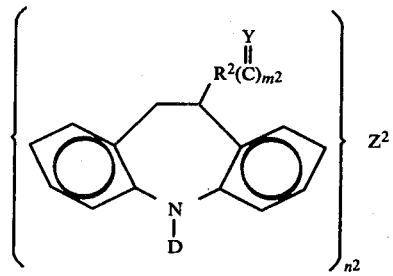

wherein:
D is 3-dimethylaminopropylene;
$m^2$ is 0 or 1;
$R^2$ is alkylene of from 1 to 7 carbon atoms;
$Z^2$ is poly(amino acid); and
$n^2$ is at least 1 and not greater than the molecular weight of $Z^2$ divided by 500.

6. Compound according to claim 5, wherein $Z^2$ is an enzyme and $n^2$ is in the range of 2 to 16.

7. Compound according to claim 6, wherein said enzyme is glucose-6-phosphate dehydrogenase.

8. Compound according to claim 5, wherein $Z^2$ is an antigen and $n^2$ is in the range of 2 to 500.

9. Compound according to claim 8, wherein said antigen is a globulin.

10. Compound according to claim 8, wherein said antigen is an albumin.

11. The conjugate of 10-(3'-carboxypropyl)-5-(3'-dimethylaminopropyl)-10,11-dihydro-5H-dibenz[b,f]-azepine with glucose-6-phosphate dehydrogenase.

12. The conjugate of 10-(3'-carboxypropyl)-5-(3'-dimethylaminopropyl)-10,11-dihydro-5H-dibenz[b,f]-azepine with a poly(amino acid) antigen.

13. Conjugate according to claim 12, wherein said antigen is a globulin.

14. Conjugate according to claim 12, wherein said antigen is an albumin.

15. Antibodies prepared in response to an antigen according to any of claims 5, 8 and 12 to 14.

* * * * *